United States Patent [19]

Eschbach

[11] Patent Number: 5,357,783
[45] Date of Patent: * Oct. 25, 1994

[54] DYNAMIC SHEAR RHEOMETER AND METHOD

[75] Inventor: Alan R. Eschbach, Hampton, N.J.

[73] Assignee: Rheometrics, Inc., Piscataway, N.J.

[ * ] Notice: The portion of the term of this patent subsequent to Dec. 21, 2010 has been disclaimed.

[21] Appl. No.: 135,648

[22] Filed: Oct. 14, 1993

Related U.S. Application Data

[63] Continuation of Ser. No. 803,948, Dec. 6, 1991, Pat. No. 5,271,266.

[51] Int. Cl.⁵ ............................................ G01N 11/02
[52] U.S. Cl. .................................................. 73/54.33
[58] Field of Search ...... 73/54.28, 54.29, 54.31–54.34, 73/54.39, 843; 374/46–48, 53

[56] References Cited

U.S. PATENT DOCUMENTS

| | | |
|---|---|---|
| 3,282,091 | 11/1966 | Webb . |
| 3,292,422 | 12/1966 | Banks . |
| 3,818,750 | 6/1974 | Karper et al. . |
| 4,552,025 | 11/1985 | Barker et al. . |
| 5,271,266 | 12/1993 | Eschbach ........................... 73/54.33 |

FOREIGN PATENT DOCUMENTS 1126995 9/1968 United Kingdom .

Primary Examiner—Robert Raevis
Attorney, Agent, or Firm—Samuelson & Jacob

[57] ABSTRACT

An improvement in a rheometer and the method for measuring rheological properties of a viscoelastic test specimen at different temperatures, at which different temperatures the viscoelastic properties exhibit a relatively wide difference, wherein the test specimen is placed between and is coupled with opposed plates, one of the opposed plates is oscillated angularly relative the other of the opposed plates, and the angular displacement of one of the plates relative to the other of the plates and the torque associated with the relative angular displacement are measured within an optimum range of torque and angular displacement for determining the rheological properties, couples a first contact area on one of the opposed plates with the test specimen when the test specimen is at one of the different temperatures, and couples a second contact area on the one of the opposed plates with the test specimen when the test specimen is at another of the different temperatures, the first contact area being different from the second contact area such that, by virtue of the difference between the first and second contact areas, the torque and the relative angular displacement measured at each of the one and the another of the different temperatures fall within the optimum range.

8 Claims, 2 Drawing Sheets

DYNAMIC SHEAR RHEOMETER AND METHOD

This is a continuation of application Ser. No. 07/803,948, file Dec. 6, 1991, now U.S. Pat. No. 5,271,266.

The present invention relates generally to the measurement of rheological properties of viscoelastic materials and pertains, more specifically, to an improvement in dynamic shear rheometers and methods which facilitate such measurements over a relatively wide range of temperature, where the rheological properties vary considerably over the relatively wide range of temperature.

Dynamic shear rheometers have been in use for some time as a tool for research and development as well as for quality control in the manufacture of a wide range of materials. In the use of such rheometers, a small sample of a viscoelastic material is placed between two parallel circular plates spaced apart by a relatively small distance. One of the plates is oscillated to vary the angular position of the plate relative to the other plate with a torque provided by a precision electronic motor, under the control of a computer, and the angular displacement of the one plate relative to the other is measured precisely, usually by an optical encoder. The rheological properties of the material then are calculated by the computer, using the known torque and angular displacement. In order to maintain accuracy, the measurement of the torque and the angular displacement are maintained within an optimum range, within which range the quantities being measured are large enough to attain adequate resolution, yet are not so large as to be outside the range of accuracy of the measuring devices employed to determine both the torque and the angular displacement. Moreover, the measurement of torque and angular displacement must be carried out within the range where the relationship between stress and strain in the material being tested remains linear.

Accordingly, where it is desired to measure rheological properties of materials over a relatively wide range of temperatures, with the properties varying considerably over the wide range of temperatures, it has been necessary either to modify the instrument, as the instrument is utilized, for accommodating the large differences in the measurements taken at the different temperatures, or to utilize different instruments for the different measurements. One such material is asphalt, where the viscoelastic properties must be measured at relatively low temperatures, where the asphalt is very stiff and requires high torques in order to attain minimal angular displacements, and at relatively high temperatures, where the asphalt is less viscous and large angular displacements are obtained with relatively low torques. The modification of an instrument to accommodate such different conditions requires time and skill and therefore impedes the effective conduct of multiple measurements by relatively unskilled operators. The utilization of multiple instruments, while being quicker and easier, requires greater expense in obtaining and maintaining the multiple instruments.

The present invention overcomes the above-outlined problem and provides an improvement which exhibits several objects and advantages, some of which are summarized as follows: Enables the accurate measurement of rheological properties of viscoelastic materials over a relatively wide range of temperature, even where the properties vary considerably over the wide range of temperature; facilitates the measurement in a single instrument, without the necessity for time-consuming changeover of the instrument and without the need for highly skilled operators; enables the use of a single sample of the material for testing in a single instrument at widely varied temperatures; facilitates sample handling, preparation and disposal, especially where the viscoelastic properties of the sample vary greatly over the range of temperatures encountered in the test procedure; provides increased accuracy with increased speed in the measurement of the viscoelastic properties of materials such as asphalt, where the properties vary considerably with variations in temperature, with economy and without the requirement for highly skilled operators; enables the economical measurement of the viscoelastic properties of materials such as asphalt in the field for exemplary control of quality with minimal effort and expense.

The above objects and advantages, as well as further objects and advantages, are attained by the present invention which may be described briefly as an improvement in a rheometer and in the method for measuring rheological properties of a viscoelastic test specimen at different temperatures, at which different temperatures the viscoelastic properties exhibit a relatively wide difference, wherein the test specimen is placed between and is coupled with opposed plates, one of the opposed plates is oscillated angularly relative to the other of the opposed plates and the angular displacement of one of the plates relative to the other of the plates and the torque associated with the relative angular displacement are measured within a predetermined optimum range of torque and angular displacement for determining the rheological properties, the improvement comprising: means for and the step of coupling a first contact surface on one of the opposed plates with the test specimen when the test specimen is at one of the different temperatures to establish a first contact area between the one of the opposed plates and the test specimen; and means for and the step of coupling a second contact surface on said one of the opposed plates with the test specimen when the test specimen is at another of the different temperatures to establish a second contact area between the one of the opposed plates and the test specimen; the first contact area being different in area from the second contact area such that, by virtue of the difference between the first and second contact areas, the torque and the relative angular displacement measured at each of said one and said another of the different temperatures fall within the predetermined optimum range.

The invention will be understood more fully, while still further objects and advantages will become apparent, in the following detailed description of preferred embodiments of the invention illustrated in the accompanying drawing, in which.

Figure 1:
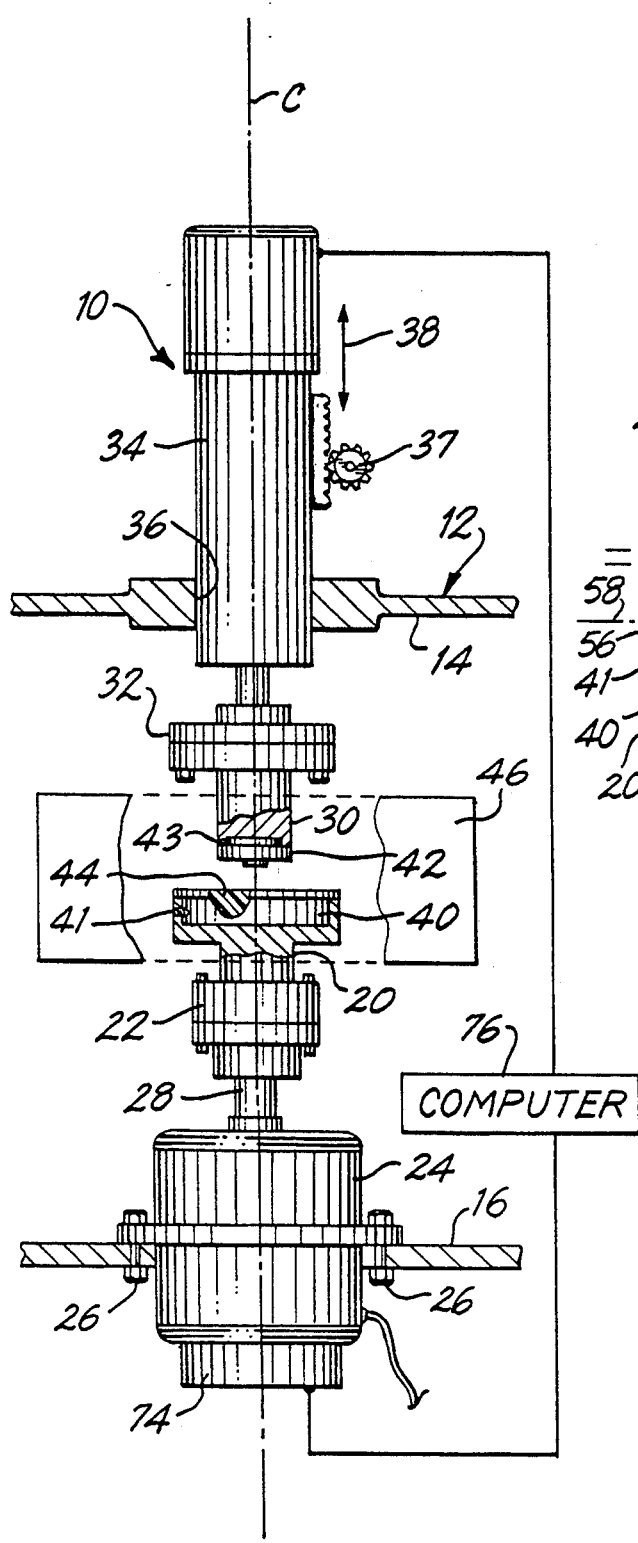
FIG. 1 is an elevational, partially sectioned and partially diagrammatic view illustrating an apparatus constructed in accordance with the invention.

Referring now to the drawing, and especially to FIG. 1 thereof, a rheometer constructed in accordance with the invention is illustrated generally at 10 and is seen to include a frame 12 having an upper support member 14 and a lower support member 16. A lower spindle 20 is coupled, by means of a lower coupling 22, to an electronic motor 24 mounted upon lower support member 16 by means of bolts 26. Lower coupling 22 is secured to drive shaft 28 of motor 24. An upper spindle 30 is coupled, by means of an upper coupling 32, to a torque-measuring transducer 34 which is received within a bore 36 in the upper support member 14 and is slidable within the bore 36 in response to the selective operation of means in the form of a rack and pinion arrangement 37 for selective axially upward and downward movement relative to frame 12, in directions parallel to a central axis C, as depicted by the arrow 38, between a retracted position, illustrated in FIG. 1, and advanced positions, as will be described below in connection with FIGS. 4 and 5. Lower spindle 20 carries a lower plate in the form of a cylindrical cup 40, secured for rotation with the spindle 20 by a set screw 41, and upper spindle 30 carries an opposed upper plate in the form of a cylindrical disk 42, secured to the spindle 30 by a set screw 43. A test specimen 44 of a viscoelastic material, such as asphalt, is placed in the cup 40 and confronts the disk 42. An environmental chamber 46 surrounds the opposed cup 40, with the test specimen 44 therein, and the disk 42 for maintaining the test specimen 44 at a selected temperature. Both the cup 40 and the disk 42 are selectively removable from the respective spindles 20 and 30 by an operator for loading, as will be described in greater detail below.

Figure 2:
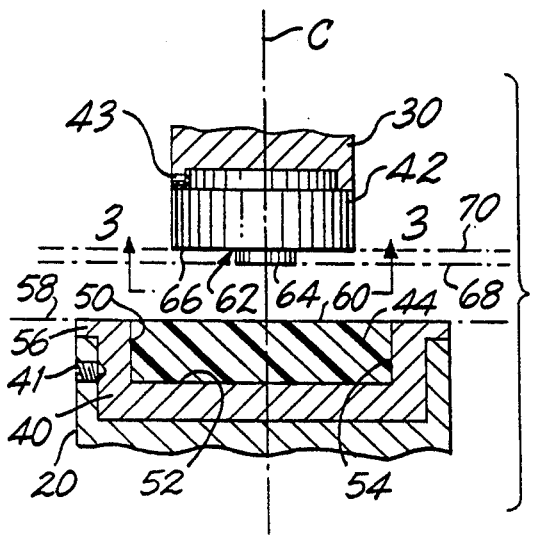
FIG. 2 is an enlarged, fragmentary elevational view of a portion of FIG. 1.
Figure 3:
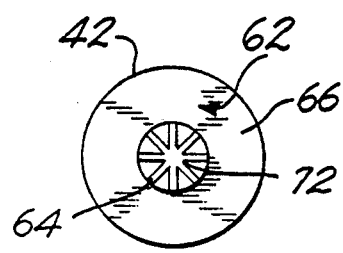
FIG. 3 is a plan view taken in the direction shown by line 3—3 of FIG. 2.

As best seen in FIGS. 2 and 3, cup 40 includes a reservoir 50 having a radially extending bottom 52 and an axially extending cylindrical side wall 54. Side wall 54 is parallel to the central axis C of the motor 24 and the transducer 34, and bottom 52 is perpendicular to the axis C. An upper flange 56 on the cup 40 locates the cup 40 accurately on the lower spindle 20 and defines a radial plane 58 which is parallel to the bottom 52 and within which the top surface 60 of the test specimen 44 lies. Disk 42 has a lower surface 62 which extends radially across the disk 42 and includes a first contact surface 64 and a second contact surface 66. Contact surfaces 64 and 66 are generally planar, with first contact surface 64 lying in a radial plane 68 and second contact surface 66 lying in a radial plane 70 parallel to and spaced axially a short distance upwardly from radial plane 68. Both radial planes 68 and 70 are parallel to plane 58 so that lower surface 62 of disk 42 confronts and is parallel to top surface 60 of the test specimen 44. Both the cup 40 and the disk 42 are centered for rotation about the axis C.

Figure 4:
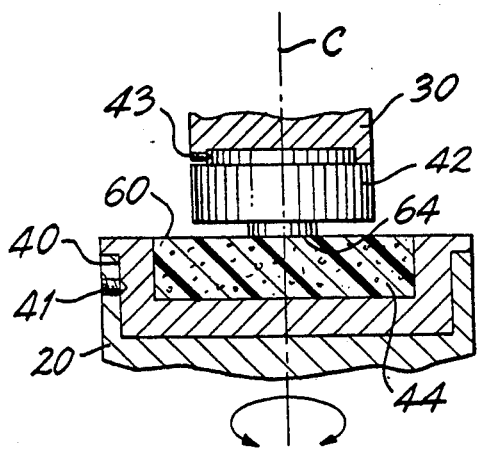
FIG. 4 is a view similar to FIG. 2, but with the component parts shown in another operating position to illustrate the method of the present invention.

When it is desired to measure rheological properties of the test specimen 44 at a first, relatively low temperature, which for an asphalt test specimen is about minus thirty degrees Fahrenheit, the temperature of the test specimen 44 is stabilized at that temperature by the environmental chamber 46 and the transducer 34 is advanced until the disk 42 is lowered to the position where the first contact surface 64 is Coupled with the test specimen 44 at the top surface 60 of the test specimen 44, as illustrated in FIG. 4. As best seen in FIG. 3, such coupling of the first contact surface 64 with the test specimen 44 preferably is enhanced by the use of coupling enhancing means shown in the form of serrations 72 on the first contact surface 64. Once the first contact surface 64 is coupled with the test specimen 44, motor 24 is operated to oscillate the cup 40, thereby inducing a torque upon disk 42. The magnitude of the torque and the relative angular displacement between the cup 40 and the disk 42 about axis C are detected by measuring means which include the transducer 34 and an angular displacement transducer 74, and the torque and angular displacement measurements are employed to calculate the rheological properties, as by a computer 76.

Figure 5:
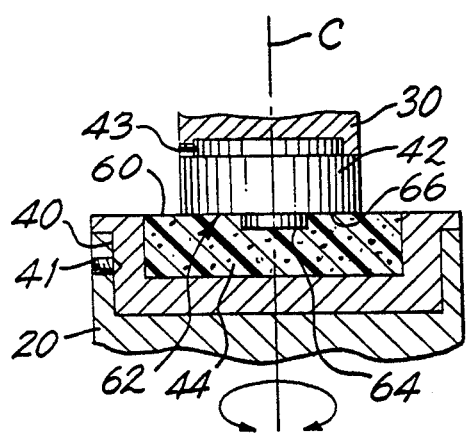
FIG. 5 is a view similar to FIG. 4, but with the component parts shown in still another operating position.

When it is desired to measure rheological properties of the test specimen 44 at a second, relatively high temperature, which for an asphalt test specimen is about one-hundred-twenty degrees Fahrenheit, the temperature of the same test specimen 44 is stabilized at the requisite temperature by the environmental chamber 46 and the transducer 34 is advanced until the disk 42 is lowered to the position where the second contact surface 66 is coupled with the test specimen 44, as well as the first contact surface 64, as illustrated in FIG. 5. Then, with both the first and second contact surfaces 64 and 66 coupled with the test specimen 44, the motor 24 is operated to oscillate the cup 40, as before, thereby inducing a torque upon the disk 42. The magnitude of the torque and the relative angular displacement between the cup 40 and the disk 42 about axis C are detected by the measuring means provided by the transducer 34 and the transducer 74, and the torque and angular displacement measurements are employed to calculate the rheological properties, as by computer 76.

The relative dimensions of the first contact surface 64 and the second contact surface 66 are selected so that the torques and the angular displacements measured by the measuring means provided by the transducers 34 and 74 at the first and second temperatures remain within a predetermined optimum range. The predetermined optimum range includes a range of measurement of torque and angular displacement for which transducers 34 and 74 are constructed to provide the greatest accuracy. The predetermined optimum range assures that the torques and the angular displacements measured by the transducers 34 and 74 are great enough to provide the degree of resolution necessary for accuracy, while not so great as to extend beyond the range of accuracy of the transducers 34 and 74. Further, the predetermined optimum range assures that the linear relationship between stress and strain in the test specimen is maintained. By such a selection of relative dimensions, and the selective coupling of disk 42 with test specimen 44 through a smaller total contact area provided by contact surface 64 at the lower temperature and through a larger total contact area provided by contact surfaces 643 and 66 at the higher temperature, the torques and angular displacements are maintained within the predetermined optimum range, that is, within the optimum range of measurement of the transducers 34 and 74, and within the linear relationship between stress and strain in the test specimen 44, despite the relatively large change in the viscosity of the test specimen 44 resulting from the difference between the first and the second temperatures. Thus, the larger total contact area compensates for the lowered viscosity to bring the torques and angular displacements within the optimum range of measurement. For a typical test of an asphalt test specimen 44, disk 42 is provided with a first contact surface 64 having an overall diameter of about eight millimeters, while second contact surface 66 has an overall diameter of about twenty-five millimeters and the axial spacing between the first and second contact surfaces 64 and 66 is about three millimeters. The inside diameter of the reservoir 50 of the cup 40 has a diameter of about forty millimeters and an axial depth of about eight millimeters and provides test specimen 44 with a volume and dimensions which enable coupling of the test specimen 44 with the cup 40 for appropriate execution of the abovedescribed procedure. In this manner, the same transducers 34 and 74 in the same rheometer 10 operate on the same test specimen 44 to obtain information concerning the rheological properties of the test specimen 44 at much different temperatures, quickly and effectively, without the necessity for multiple test specimens, or multiple manipulations of separate test specimens, or the placement of the same test specimen in multiple rheometers. It is noted that although in the illustrated embodiment of rheometer 10 the torque and angular displacement measurements are shown to be accomplished by separate transducers 34 and 74, an integrated transducer assembly can be utilized to accomplish the same measurements.

Figure 6:
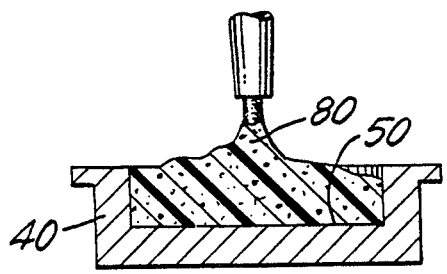
FIGS. 6 through 8 are elevational cross-sectional views illustrating a procedural step in the use of the apparatus of the invention.
Figure 7:
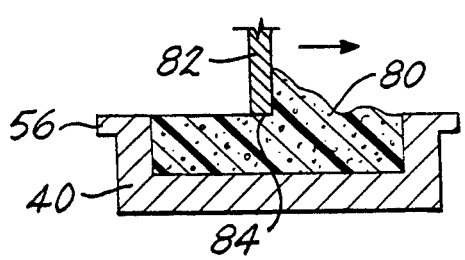
Figure 8:
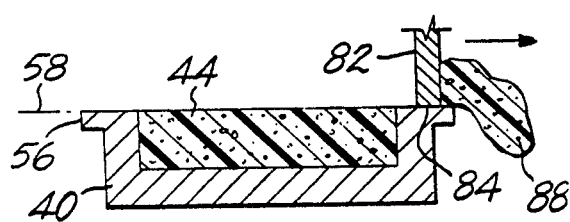

The use of cup 40 as the lower plate of a parallel plate type rheometer simplifies the test procedure to the point where operators of limited skill can perform the required tests in the field. As shown in FIGS. 6 through 8, loading of the cup 40 with a sample of asphalt is a simple matter. Cup 40 is first filled with molten asphalt 80, as illustrated in FIG. 6, with the cup 40 removed from the rheometer 10. Subsequently, the asphalt 80 in the cup 40 is leveled, as by drawing an implement 82 having a straight edge 84 along the surface of the asphalt 80, as seen in FIG. 7, the straight edge 84 being guided by the upper surface 86 of the flange 56 of the cup 40 to assure that excess asphalt 88 is removed and the remaining asphalt test specimen 44 includes the level top surface 60, placed in plane 58, as illustrated in FIG. 8. Once prepared, the cup 40, with the test specimen 44 in the cup 40, is easy to handle and can be inserted readily into the rheometer 10 and subsequently removed without making direct contact with the asphalt. Further, any desired preconditioning of the asphalt test specimen 44 is accomplished readily while the test specimen 44 is removed from the rheometer 10. Additionally, the test sample 44 itself is disposed of without difficulty.

It will be seen that the present invention attains the objects and advantages summarized above; namely: Enables the accurate measurement of rheological properties of viscoelastic materials over a relatively wide range of temperature, even where the properties vary considerably over the wide range of temperature; facilitates the measurement in a single instrument, without the necessity for time-consuming changeover of the instrument and without the need for highly skilled operators; enables the use of a single sample of the material for testing in a single instrument at widely varied temperatures; facilitates sample handling, preparation and disposal, especially where the viscoelastic properties of the sample vary greatly over the range of temperatures encountered in the test procedure; provides increased accuracy with increased speed in the measurement of the viscoelastic properties of materials such as asphalt, where the properties vary considerably with variations in temperature, with economy and without the requirement for highly skilled operators; enables the economical measurement of the viscoelastic properties of materials such as asphalt in the field for exemplary control of quality with minimal effort and expense.

It is to be understood that the above detailed description of preferred embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. An improvement in an apparatus for measuring rheological properties of a viscoelastic test specimen at different temperatures, at which different temperatures the viscoelastic properties exhibit a relatively wide difference, wherein the test specimen is placed between and coupled with opposed plates, one of the opposed plates is oscillated angularly relative to the other of the opposed plates, and the angular displacement of one of the plates relative to the other of the plates and the torque associated with the relative angular displacement are measured by measuring means within a predetermined range of measurement of torque and angular displacement for determining the rheological properties, the improvement comprising:
   a first contact surface on one of the opposed plates for being coupled with the test specimen when the test specimen is at one of the different temperatures;
   a second contact surface on said one of the opposed plates for being coupled with the test specimen when the test specimen is at another of the different temperatures; and
   selective coupling means for selectively coupling the first contact surface with the test specimen to establish a first contact area between said one of the opposed plates and the test specimen when the test specimen is at said one of the different temperatures and is coupled with the other of the opposed plates, said selective coupling means including further means for effecting relative movement between the second contact surface and the test specimen in a direction essentially normal to said angular displacement to selectively couple the second contact surface with the test specimen to establish a second contact area between said one of the opposed plates and the test specimen when the test specimen is at said another of the different temperatures and is coupled with the other of the opposed plates;
   the first contact area being different in area from the second contact area such that, by virtue of the difference in area between the first and second contact areas, the torque and the relative angular displacement measured by the measuring means at each of said one and said another of the different temperatures fall within the predetermined range.

2. The improvement of claim 1 wherein the different temperatures include a first temperature and a second temperature, the first temperature is lower than the second temperature, and the first contact area is less in area than the second contact area.

3. The improvement of claim 1 wherein the opposed plates are oscillated angularly about an axis extending in said direction essentially normal to said angular displacement, the first and second contact surfaces extend radially along the said one of the opposed plates, and the first contact surface is spaced axially, in the direction of said axis, from the second contact surface, the selective coupling means, and said further means thereof, including means for effecting selective relative axial movement, along the direction of said axis, between said one of the opposed plates and the test specimen to establish said first and second contact areas.

4. The improvement of claim 3 wherein the different temperatures include a first temperature and a second temperature, the first temperature is lower than the second temperature, the first contact area is less in area than the second contact area and the first contact surface is closer to the other of the opposed plates than is the second contact surface.

5. An improvement in the method for measuring rheological properties of a viscoelastic test specimen at different temperatures, at which different temperatures the viscoelastic properties exhibit a relatively wide difference, wherein the test specimen is placed between and is coupled with opposed plates, one of the opposed plates is oscillated angularly relative to the other of the opposed plates, and the angular displacement of one of the plates relative to the other of the plates and the torque associated with the relative angular displacement are measured within a predetermined range of torque and angular displacement for determining the rheological properties, the improvement comprising:

selectively coupling a first contact surface on one of the opposed plates with the test specimen to establish a first contact area between said one of the opposed plates and the test specimen when the test specimen is at one of the different temperatures; and selectively coupling a second contact surface on said one of the opposed plates with the test specimen by effecting relative movement between the second contact surface and the test specimen in a direction essentially normal to said angular displacement to establish a second contact area between said one of the opposed plates and the test specimen when the test specimen is at another of the different temperatures;

the first contact area being different in area from the second contact area such that, by virtue of the difference in area between the first and second contact areas, the torque and the relative angular displacement measured at each of said one and said another of the different temperatures fall within the predetermined range.

6. The improvement of claim 5 wherein the different temperatures include a first temperature and a second temperature, the first temperature is lower than the second temperature, and the first contact area is less in area than the second contact area.

7. An apparatus for measuring rheological properties of a viscoelastic test specimen at different temperatures, at which different temperatures the viscoelastic properties exhibit a relatively wide difference, the apparatus comprising:

a cup having a reservoir for receiving the test specimen;

a disk opposed to the cup and having a first contact surface for being coupled with the test specimen in the reservoir of the cup to couple the disk with the cup when the test specimen is at one of the different temperatures, and a second contact surface confronting the reservoir in the cup for being coupled with the test specimen in the reservoir of the cup to couple the disk with the cup when the test specimen is at another of the different temperatures;

moving means for causing relative angular oscillation between the disk and the cup about an axis when the disk is coupled with the cup through the test specimen so as to induce relative angular displacement between the disk and the cup about the axis, and a torque associated with the relative angular displacement;

measuring means for measuring the relative angular displacement between the disk and the cup and for measuring the torque associated with the relative angular displacement within a predetermined range for determining the rheological properties of the test specimen; and selective coupling means for selectively coupling the first contact surface with the test specimen to establish a first contact area between the disk and the test specimen when the test specimen is at said one of the different temperatures and is coupled with the cup, said selective coupling means including further means for effecting relative movement between the second contact surface and the test specimen in a direction essentially normal to said angular displacement to selectively couple the second contact surface with the test specimen to establish a second contact area between the disk and the test specimen when the test specimen is at said another of the different temperatures and is coupled with the cup;

the first contact area being different in area from the second contact area such that, by virtue of the difference in area between the first and second contact areas, the torque and the relative angular displacement measured by the measuring means at each of said one and said another of the different temperatures fall within the predetermined range.

8. The apparatus of claim 7 wherein the different temperatures include a first temperature and a second temperature, the first temperature is lower than the second temperature, and the first contact area is less in area than the second contact area.

* * * * *